United States Patent [19]

Vogel et al.

[11] Patent Number: 4,816,224
[45] Date of Patent: Mar. 28, 1989

[54] DEVICE FOR SEPARATING PLASMA OR SERUM FROM WHOLE BLOOD AND ANALYZING THE SAME

[75] Inventors: Peter Vogel; Hans-Peter Braun, both of Hemsbach; Dieter Berger, Viernheim; Wolfgang Werner, Mannheim, all of Fed. Rep. of Germany

[73] Assignee: Boehringer Mannheim GmbH, Mannheim, Fed. Rep. of Germany

[21] Appl. No.: 81,624

[22] Filed: Jul. 31, 1987

Related U.S. Application Data

[60] Continuation of Ser. No. 608,991, May 10, 1984, abandoned, which is a division of Ser. No. 289,943, Aug. 4, 1981, Pat. No. 4,477,575.

[30] Foreign Application Priority Data

Aug. 5, 1980 [DE] Fed. Rep. of Germany ....... 3029579

[51] Int. Cl.$^4$ .................. G01N 21/77; G01N 33/52
[52] U.S. Cl. .................. 422/55; 210/767; 210/505; 210/509; 422/56; 422/57; 422/58; 422/101; 436/170; 436/177
[58] Field of Search .................. 422/55–58, 422/101; 436/170, 177, 178; 73/64.1; 210/500.1, 503, 505, 508, 509, 767, 782, 927

[56] References Cited

U.S. PATENT DOCUMENTS

| | | |
|---|---|---|
| 3,036,894 | 5/1962 | Forestiere .................. 422/66 |
| 3,092,465 | 6/1963 | Adams et al. . |
| 3,260,413 | 7/1966 | Natelson .................. 422/66 X |
| 3,552,928 | 1/1971 | Fetter .................. 422/56 |
| 3,579,303 | 5/1971 | Pickering .................. 422/102 X |
| 3,630,957 | 12/1971 | Rey et al. .................. 252/408 |
| 3,663,374 | 5/1972 | Moyer et al. . |
| 3,937,860 | 2/1976 | Gusman et al. .................. 210/500.1 X |
| 4,012,325 | 3/1977 | Columbus .................. 210/516 |
| 4,069,017 | 1/1978 | Wu et al. .................. 422/56 X |
| 4,144,306 | 3/1979 | Figueras .................. 436/95 X |
| 4,223,089 | 9/1980 | Rothe et al. .................. 422/56 X |
| 4,234,317 | 11/1980 | Lucas et al. .................. 422/101 X |
| 4,246,107 | 1/1981 | Takenaka et al. .................. 210/806 |
| 4,256,693 | 3/1981 | Kondo et al. .................. 422/56 |
| 4,292,272 | 9/1981 | Kitajima et al. .................. 422/56 X |
| 4,312,834 | 1/1982 | Vogel et al. .................. 422/56 |
| 4,330,410 | 5/1982 | Takenaka et al. .................. 210/767 |

OTHER PUBLICATIONS

Averso, American Laboratory, vol. 8, No. 4, (Apr. 1976), pp. 97, 98, 101, 102, 104.

*Primary Examiner*—Barry S. Richman
*Assistant Examiner*—Robert J. Hill, Jr.
*Attorney, Agent, or Firm*—Felfe & Lynch

[57] ABSTRACT

A device for separating plasma or serum from whole blood and analyzing the same, wherein the device includes a layer of glass fibers with an average diameter of from 0.2 to 5 microns and having a density of from 0.1 to 0.5 g./cm$^3$ and an adsorption volume at least twice that of the plasma or serum to be separated and, preferably, more than 3.3 times the volume.

10 Claims, 8 Drawing Sheets

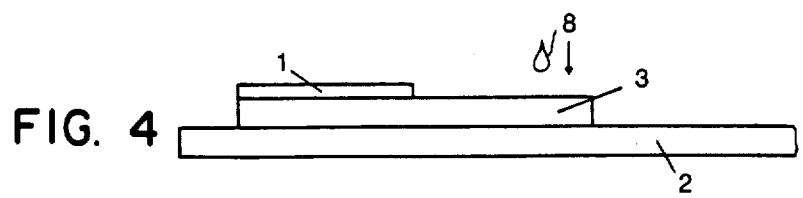
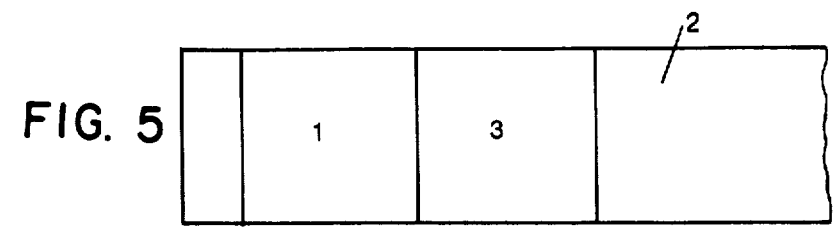
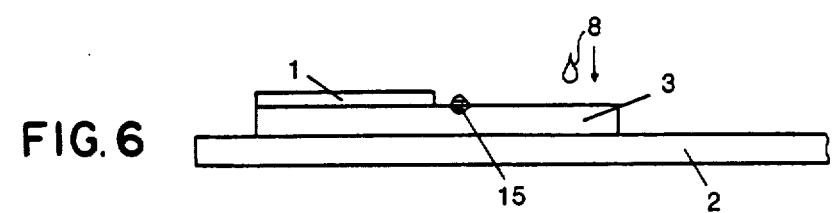
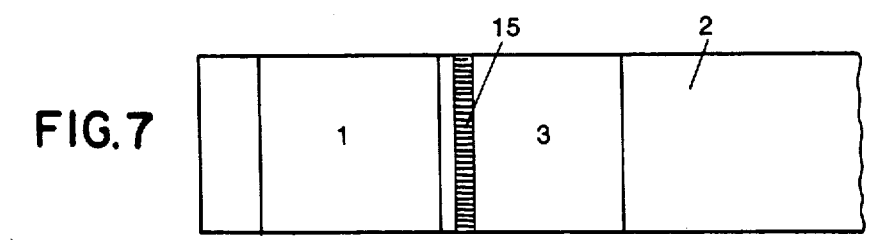
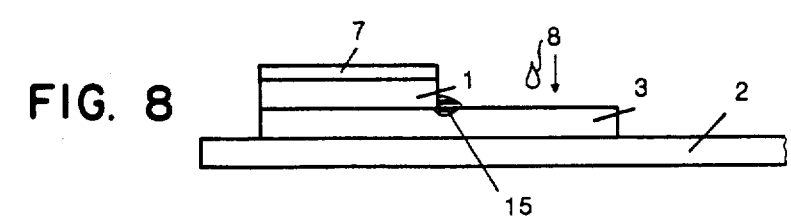

//  4,816,224

DEVICE FOR SEPARATING PLASMA OR SERUM FROM WHOLE BLOOD AND ANALYZING THE SAME

This application is a continuation of application Ser. No. 608,991, filed May 10, 1984, now abandoned, which in turn is a divisional of application Ser. No. 289,943, filed Aug. 4, 1981 and now U.S. Pat. No. 4,477,575, which was issued Oct. 16, 1984.

BACKGROUND OF THE INVENTION

This invention relates to a device for separating plasma or serum from whole blood.

In clinical chemistry, the separation of serum or plasma from whole blood is of outstanding importance since, in practice, it is not possible to carry out the analysis of dissolved blood components without disturbances unless the separation takes place.

The normal and most conventional manner of separating serum or plasma from erythrocytes is centrifuging. Centrifugation, however, causes problems with respect to separating supernatant and blood cake. This problem is particularly acute when small amounts are involved. To that end, a whole series of adjuvants have been described in the literature. See, in this regard, Federal Republic of Germany Patent Specification No. 25 59 242 (U.S. Pat. No. 4,012,325).

The use of whole blood in the case of rapid diagnostic agents gives rise to special problems. Rapid diagnostic agents are reagent-containing carriers, which are absorbent or swellable. Preferably, they are made of filter paper. In use, one applies a small amount, such as a droplet, of the liquid to be investigated to the carrier. After a short period of time to allow reactions to take place, a color change occurs, which can be evaluated visually or via remission photometry. Since turbid or coloured solutions, such as blood, disturb the readings, attempts have, therefore, been made to make rapid diagnostics available for the direct use of whole blood. Thus, for example, mention may be made of the coating of test papers with semi-permeable membranes (see U.S. Pat. No. 3,092,465) and the use of swellable films into which only the dissolved components of the blood can penetrate but not the erythrocytes (see Federal Republic of Germany Patent Specification No. 15 98 153; U.S. Pat. No. 3,630,957). These two methods are per se usable but only for tests for low molecular weight components of blood, for example glucose or urea. Higher molecular weight components of the blood, such as lipids, or substrates bound to serum protein, such as bilirubin, cannot be determined in this way because they are not able to penetrate into the film or to pass through the semipermeable membrane. Furthermore, suggestions have been made for covering diagnostic agents with membrane filters for separating off the blood cells (see Federal Republic of Germany Patent Specifications Nos. 22 22 951 and 29 22 958 which correspond to U.S. Pat. Nos. 3,663,374 and 4,256,693). A disadvantage of these diagnostic agents is that the blood can only penetrate through the membrane filter very slowly and in small amounts because the membrane is very easily blocked up. This results in a reaction which takes longer than is desired. In contradistinction to the previously-mentioned diagnostic agents, which are already commercially available, "rapid tests" of the last-mentioned type have not yet been marketed.

Federal Republic of Germany Patent Specification Nos. 29 08 721 and 29 08 722 which correspond to U.S. Pat. Nos. 4,246,107 and 4,330,410, teach that lymphocytes and leukocytes can be separated from blood when blood is filtered through a layer of synthetic resin fibres with an average fibre diameter of 5 to $20\mu$ (lymphocytes) or of 3 to $10\mu$ (leukocytes). However, since the erythrocytes preponderantly pass through the filter with the plasma, these filters are not suitable for obtaining plasma. Furthermore, carbon fibres, glass fibres and metal fibres are mentioned purely speculatively.

SUMMARY OF THE INVENTION

Therefore, it is an object of the present invention to provide a simple means for separating plasma or serum from whole blood which separates small amounts of blood quickly and without centrifuging and is especially suitable for preparing samples for diagnostic purposes.

It has now been found that the separation of plasma or serum from whole blood takes place quickly and simply and in sufficient amount when the blood is allowed to run through a packing of glass fibres alone or in admixture with other fibres. This must be regarded as being surprising since, in the above-mentioned Federal Republic of Germany Patent Specification No. 22 22 951, the use of glass fibre mats has already been described for the separation of white corpuscles but, in order to separate erythrocytes, this reference teaches that a membrane filter is absolutely necessary.

Thus, this invention teaches a device useful in separating plasma or serum from whole blood, comprising a layer of glass fibres with a diameter of 0.2 to $5\mu$, preferably of 0.5 to $2.5\mu$, and especially of 0.5 to $1.5\mu$ and with a density of 0.1 to 0.5 g./cm$^3$, the volume of the lasma or serum to be separated being at most 50% and preferably less than 30% of the absorption volume of the glass fibre layer; i.e., the absorption volume of the glass fibre layer is at least two times and preferably more than 3.3 times the volume of the plasma or serum separated from the whole blood.

The glass fibres can be in loosely stapled form, or can also be in the form of papers, fleece or felts or can also be formed in any desired shape when held by a forming body.

Rapid diagnostic devices which use the thus described formed glass fibres can be used with whole blood. Previously, it was necessary to obtain serum or plasma from whole blood in order to use a rapid diagnostic agent. This is now unnecessary.

Furthermore, columns, filter funnels or other suitable vessels packed with glass fibres can also be used for obtaining serum or plasma by simply allowing whole blood to run through. This makes serum or plasma available for diagnostic agents since the serum or plasma passes through such a layer more quickly than the erythrocytes and leukocytes.

The above-mentioned glass fibres can consist of fibres of differing diameters. The glass material can consist of alkali-containing or alkaline-free boro-silicate glass or pure quartz glass. Fibre of other technical glasses, for example boron-free alkali glasses, crystal glass, lead glass and the like, are not commercially available with the necessary dimensions and could not be investigated. However, it is assumed that they are also suitable. The average diameter of the glass fibres can be from $0.2\mu$ to about $5\mu$, preferably from $0.5\mu$ to $2.5\mu$ and especially from $0.5\mu$ to $1.5\mu$. The diameters of the fibres can, depending upon their mode of production, vary very considerably but an upper limit of about 10μ should only be exceeded in exceptional circumstances. The length of the fibres is only limited by the nature of the packing. Depending upon the nature of the packing, densities of 0.1 to 0.5 and usually of 0.2 to 0.4 g./cm³ are found.

Furthermore, the glass fibres can be mixed with one another and also with other materials, the internal holding together of the fibres thereby being improved. Thus, for example, use can be made of synthetic fibres, such as of polyester, polyamide and the like, as well as fibres of polyethylene, polypropylene and other thermoplastic synthetic resins. These additional fibres can also have a larger diameter (e.g. 10 to 20μ), so long as the amount thereof is not so large that it adversely affects the seprating ability of the finer glass fibres used according to the present invention.

Furthermore, the glass fibres can be consolidated by the addition of inorganic binding agents, for example waterglass, or of organic binding agents, for example polyvinyl acetate, polyvinyl propionate, polyacrylic acid esters and the like, by means of which the glass fibres are stuck at the points of contact to the binder.

The combination of the glass fibre layers according to the prsent invention with diagnostic agents is especially preferred and is also the subject of the present invention.

In these diagnostic agents, the glass fibres can also contain reagents which prevent the haemolysis of erythrocytes, as well as reagents which inhibit or promote coagulation. The glass fibres can also contain reagents which are required in the indicator layer but are incompatible with other reagents present therein. These latter reagents can, of course, also be placed in layers which are between the glass fibres and the indicator layer.

BRIEF DESCRIPTION OF THE DRAWINGS

Preferred embodiments of the invention will now be described with reference to drawings, in which:

FIG. 4 is an elevation of a fourth preferred embodiment;

FIG. 5 is a top view of the fourth preferred embodiment shown in FIG. 4;

FIG. 6 is an elevation of a fifth preferred embodiment;

FIG. 7 is a top view of the preferred embodiment shown in FIG. 6;

FIG. 8 is an elevation of a sixth preferred embodiment;

DESCRIPTION OF THE PREFERRED EMBODIMENTS

Figure 1:
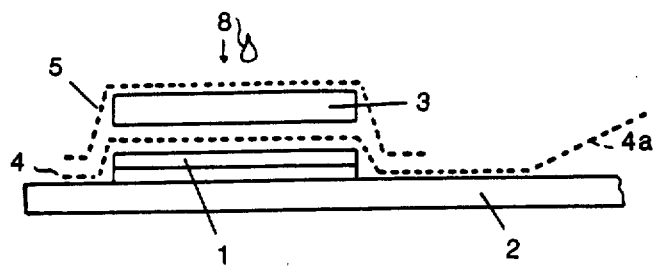
FIG. 1 is a schematic elevation of a first preferred embodiment.

The construction of one such diagnostic agents according to the present invention is illustrated in FIG. 1 of the accompanying drawings. Onto a stiff substrate 2, the reaction layer 1 is stuck. Closely above the reaction layer, a thin and inherently stable separating layer 4 is applied which is permeable to liquids. This stable separating layer consists of a meshwork of woven or felted synthetic resin fibres, is stuck on both sides of the reaction layer, and is positioned on the substrate in an easily removable manner and in such a way that an easily gripped end 4a on the longer end of the substrate remains free. Above the reaction and separating layers, a glass fibre paper 3 is applied. This is fixed in position by a further meshwork 5 which, like the separating layer 4, is stuck down on either side of the reaction layer.

The reaction layer 1 can consist of an impregnated absorbent carrier or of a swellable or porous synthetic resin film. The substrate 2 is preferably a comparatively thick synthetic resin film, a rigid cardboard, a glass plate or some other stable carrier material.

After the application of a drop of blood 8 to the upper side of the rapid diagnostic agent, the plasma is separated from erythrocytes and leukocytes in the glass fibre paper 3. The plasma separated in this manner passes via the separating layer 4 into the reaction zone or layer 1 of the diagnostic agent. After an appropriate time, during which the plasma has penetrated into the reaction zone, the free end 4a of the separating layer is gripped and the layer 4 removed, together with the glass fibre paper 3 and the meshwork 5. Subsequently, the reaction layer in which the reaction now takes place can be evaluated visually or remission photometrically.

Figure 2:
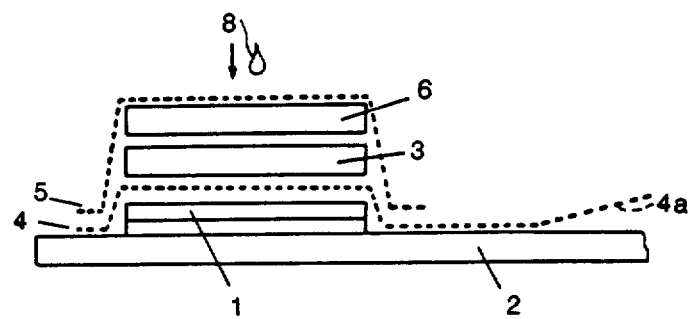
FIG. 2 is an elevation of a second preferred embodiment.
Figure 3:
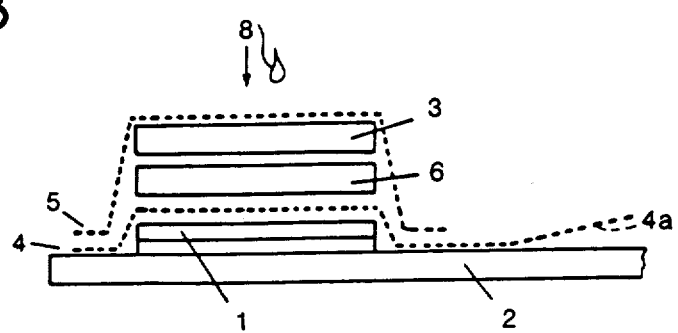
FIG. 3 is an elevation of a third preferred embodiment.

Another possible form of construction of the rapid diagnostic agent according to the present invention is illustrated in FIGS. 2 and 3. In this embodiment, in addition to the above-described construction, they have one or more layers 6 which are permeable to all kinds of liquids. These layers are applied above (FIG. 2) or below (FIG. 3) the glass fibre paper 3. These additional layers can be impregnated with reagents which are either readily soluble and, together with the plasma, pass into the reaction zone or are less soluble and allow one or more preliminary stages of the detection reaction to take place outside of the final reaction zone 1.

FIGS. 4 and 5 illustrate another construction of the rapid diagnostic agent according to the present invention, in which the glass fibre paper 3 is stuck directly on to the substrate 2. The reaction layer 1 is superposed on one zone of the glass fibre paper defined thereby. Blood 8 is applied to the other zone of the glass fibre paper which remains free. The plasma separating from the erythrocytes in the glass fibre paper diffuses in the glass fibre paper towards the reaction layer and passes into it. The colours resulting due to the reaction can be observed from the upper side of the rapid diagnostic agent and can be evaluated. The reaction layer can be applied directly to the glass fibre mat by "printing" or coating. However, it can also be stuck on to the glass fibre paper in the form of a wholly or partly impregnated absorbent carrier.

Figure 9:
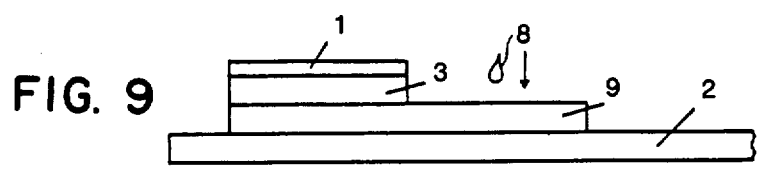
FIG. 9 is an elevation of a seventh preferred embodiment.
Figure 10:
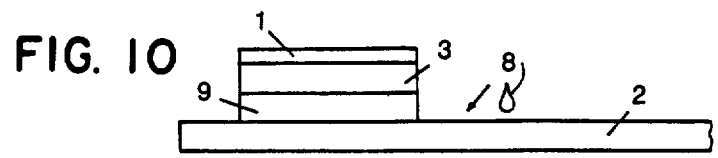
FIG. 10 is an elevation of an eighth preferred embodiment.

Furthermore, as illustrated in FIGS. 9 and 10 of the accompanying drawings, the diagnostic agent according to the present invention can be constructed in such a manner that onto the substrate 2, an absorbent material 9 is first applied, such as cellulose paper or a synthetic fibre fleece. Above this material, the glass fibre paper 3 and the reaction layer 1 are applied. The absorbent material 9 can have the same surface area as the reaction layer (FIG. 10) or can have a larger surface area so that the material 9 has an uncovered area (FIG. 9). The blood 8 is droped on to the uncovered surface area of the absorbent material (FIG. 9) or directly next to the absorbent material (FIG. 10) and rapidly taken up by this and sucked under the glass fibre paper. Subsequently, due to the absorbency of the glass fibre paper, blood is sucked upward through the glass fibre paper, separation of the erythrocytes thereby taking place, and plasma passes into the reaction layer 1. The reaction is, as in FIG. 4, observed from the upper side of the rapid diagnostic agent.

Figure 11:
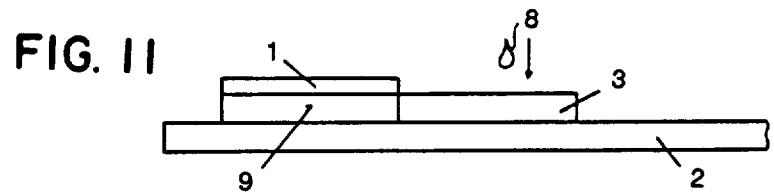
FIG. 11 is an elevation of a ninth preferred embodiment.
Figure 12:
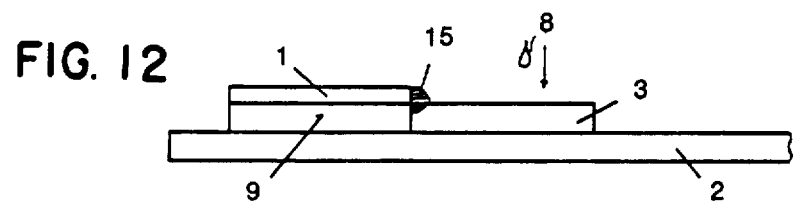
FIG. 12 is an elevation of a tenth preferred embodiment.
Figure 13:
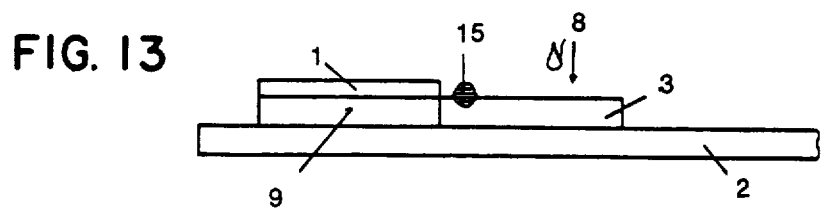
FIG. 13 is an elevation of an eleventh preferred embodiment.

FIG. 11 of the accompanying drawings illustrates yet another construction of a rapid diagnostic agent suitable for the direct use of whole blood. This figure shows an embodiment in which an absorbent layer 9 and glass fibre layer 3 are applied onto a stiff substrate 2, side by side. The absorbent layer may consist of e.g., cellulose paper or a cellulose containing synthetic fibre fleece. The two layers should be in close contact with one another. On the surface of the absorbent layer 9, reaction layer 1 the detection contains reagents needed for rapid diagnosis. These reagents can be applied, for example, by coating with an open film as described in Federal Republic of Germany Patent Specification No. 29 10 134. Upon applying a drop of blood 8 on to the side of the glass fibre layer remote from the reaction zone, the separation of plasma from erythrocytes takes place in such a manner that the plasma front first reaches the point of separation from the absorbent layer 9 and is immediately sucked up by this. Due to capillary forces, the plasma then passes into the actual reaction layer 1 where the detection reaction becomes visible, for example, by a colour change, which can be seen from above.

Figure 14:
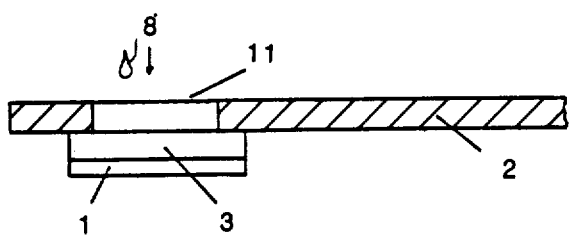
FIG. 14 is an elevation, partly in section, of a twelfth preferred embodiment.
Figure 15:
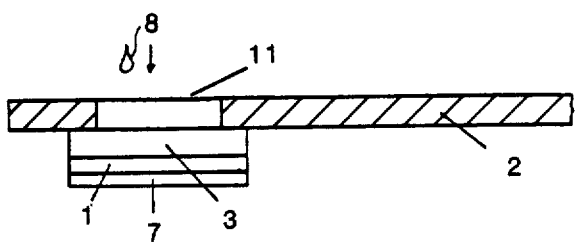
FIG. 15 is an elevation, partly in section, of a thirteenth preferred embodiment.

Further, FIG. 14 depicts another embodiment of the present invention. The glass fibre paper 3 is stuck onto a substrate 2, the substrate having one or more holes 11 at the point of contact. On the other side of the glass fibre paper, a reaction layer 1 is applied either directly or by sticking. Blood 8 is applied to the diagnostic agent in such a manner so that it can pass through the hole or holes to the glass fibre paper 3. The plasma separated in the glass fibre paper now passes to the reaction layer 1 and gives rise to a reaction which can be evaluated on the surface thereof visually or remission photometrically. The reaction layer can also be protected by a transparent covering layer 7 as shown in FIG. 15.

The reaction layer 1 can be, for example, a layer "printed" on to the glass fibre mat and can also be a multi-layer element in which the layers can contain various reagents and/or can fulfil several functions, as is described, for example, in Federal Republic of Germany Patent Specification No. 29 22 958 (U.S. Pat. No. 4,256,693).

Figure 16:
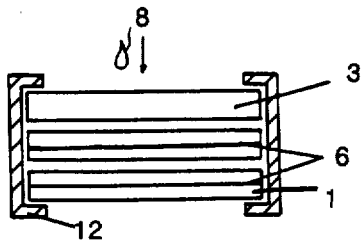
FIG. 16 is an elevation, partly in section, of a fourteenth preferred embodiment.
Figure 17:
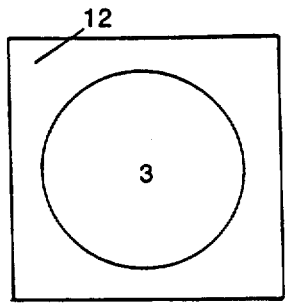
FIG. 17 is a top view of the fourteenth preferred embodiment shown in FIG. 16.

FIG. 16 of the accompanying drawings shows a side view and FIG. 17 a top view of a further construction of a diagnostic agent according to the present invention. In this embodiment the layer 3 consists of glass fibres. Additionally, one or more layers 6 necessary for the reaction can be held together by a previously produced formed body 12. The blood 8 is dropped on to the glass fibre filter side of the diagnostic agent. The separated plasma subsequently passes into the reaction layer 1 and the indicator reaction on the side opposite to the glass fibre filter can be evaluated visually or remission photometrically.

For reasons of clarity of the drawings, in some Figures (for example FIGS. 1 and 16) the various layers are, in part, shown with intermediate spaces. In practice, however, the layers lie on one another in such a manner that liquids can pass unhindered from one layer to another. Furthermore, in FIG. 16, the reaction layers 1 and 6 are illustrated as divided horizontally in order to indicate that they can also consist of several layers lying on top of one another.

Blood separation accomplished using the agents according to FIGS. 4, 5, 9 and 11 can be substantially improved when a hydrophobic barrier is applied on the glass fibres 3 beside or in the reaction layer 1 which barrier 15 partly projects into the glass fibres 3. FIGS. 6, 7, 12 and 13 show these barriers 15 but otherwise correspond in their construction to that of FIGS. 4, and 11. This barrier not only prevents blood 8 on the surface of the glass fibres from spreading out and contaminating the indicator zone, but it also decisively improves the separating action of the glass fibres. Therefore, it is possible to operate with relatively small glass fibre papers 3, the result of which is that substantially smaller amounts of blood are required. The barrier can be applied in a conventional manner, for example from nozzles or with rollers. The hydrophobic material for the barrier can be, for example, a melt adhesive, a conventional solvent adhesive or wax.

Figure 18:
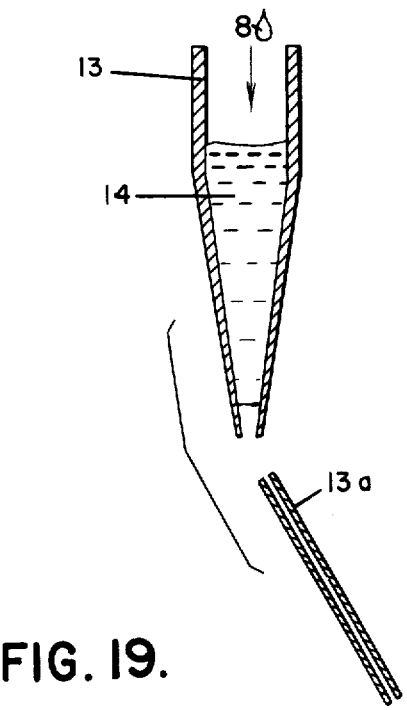
FIG. 18 is an elevation, partly in section, of a fifteenth preferred embodiment.

Furthermore, FIG. 18 of the accompanying drawings illustrates the construction of a formed body according to the present invention which separates plasma from the erythrocytes of whole blood without centrifuging and makes the plasma available for diagnostic purposes. For this purpose, a tube or a vessel 13, which has, for example, the illustrated shape, is packed with the glass fibres 14. Blood 8 is introduced into the vessel from above. On the downward path, the plasma is separated from the erythrocytes of the blood by means of the glass fibres. The plasma collecting in the lower part of the vessel 13 can now, for example, be withdrawn or sucked off through an "end-to-end" capillary 13a and used directly for diagnostic purposes.

Figure 19:
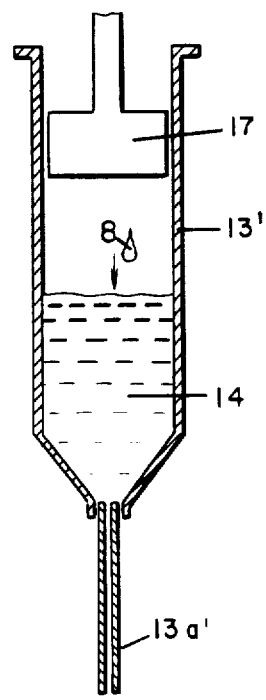
FIG. 19 is an elevation, partly in section, of a sixteenth preferred embodiment.

Another construction according to the present invention is illustrated in FIG. 19 of the accompanying drawings. In this embodiment vessel 13 appropriate for the separation of the erythrocytes has the form of a piston syringe, the lower part of which is tightly packed with glass fibres 14. The blood 8 is introduced into the open top of the vessel. After separation of plasma and erythrocytes has taken place, the plasma which collects in the lower part of the vessel can be forced out of the syringe into capillary 13a' by the insertion careful pressing of a piston 17.

Figure 20:
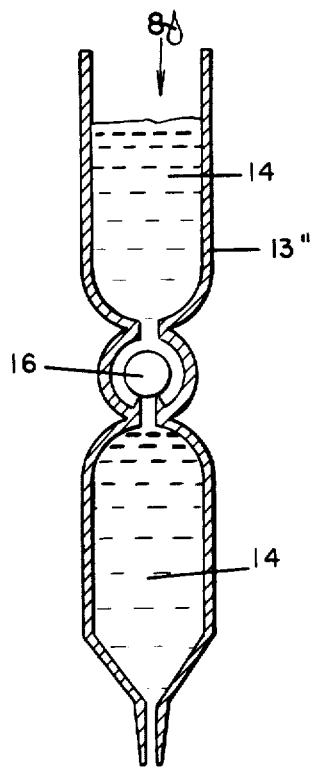
FIG. 20 is an elevation, partly in section, of a seventeenth preferred embodiment.

The process according to the present invention for obtaining plasma, as illustrated in FIG. 20 of the accompanying can also be carried out with the use of a vessel 13". It is divided into two parts by a valve 16 which operates to permit passage in one direction, the vessel 13" being packed with the above-described glass fibres 14. The blood 8 is introduced into the top of the vessel. After separation from the erythrocytes, the plasma collects in the lower part of the vessel and can then be removed by pressing together the lower part of the vessel, the valve 16 preventing the plasma from flowing back into the upper part of the vessel containing the blood cells.

Furthermore, the process according to the present invention can be carried out with an arrangement as illustrated in FIG. 1, the reaction layer 1 stuck on to the substrate 2 thereby consisting of a definite absorbent material so that, upon applying blood, a definite volume of plasma passes into the layer 1. After separation of the layers 3, 4 and 5, the plasma, i.e. the substance to be analyzed, can be eluted by a solvent. The elution of the plasma and the analysis can be carried out immediately but also, depending upon the substance to be analyzed, at some later time in another place. If the analysis is to take place later, it can be advantageous first to dry in the plasma, for example with warm air or by freeze drying. Furthermore, it is possible, separately to provide one or more zones separate from the zone for sample application which contains reagents so that, when eluting with a solvent, the whole reaction mixture is simultaneously eluted.

If the reaction colour is to be evaluated not only visually but also in a remission photometer, it is preferable to cover the reaction layer 1 with a covering layer 7 in order to avoid contamination of the measurement arrangement. If the reaction layer 1 is a film, for example as described in Federal Republic of Germany Patent Specifications Nos. 29 10 134 or 15 98 153, then it is preferable to coat this directly on to the covering layer 7 e.g. FIGS. 8, 15, and 21) and then assemble the two together to the substrate. One possible embodiment is illustrated in FIG. 8 of the accompanying drawings. Of course, the covering layer 7 can also be used in other embodiments, such as is illustrated in FIG. 15 which otherwise corresponds to the construction of FIG. 14.

It has proven to be advantageous to choose arrangements in which the reaction layer 1 is not brought into fluid-conveying contact with the glass fibre layer 3 of the absorbent layer 9 until said layers 3, 9 are completely filled with plasma or serum. The advantages of these arrangements are that the plasma or serum can be brought into contact with the reaction layer 1 at a previously determined and exact time. Furthermore, this contacting takes place over the whole surface area so that chromatographic effects, such as can occur in the case of the above arrangements, are prevented. The fact that, between the application of the blood 8 and the commencement of the reaction in the reaction layer 1, there can be a previously determined time is of great importance in the case of reactions which are to take place under specially controlled conditions. Thus, in the case of the determination of enzymes, which must take place at especially constant temperature, the reaction can first be commenced when the diagnostic agent has a sufficiently constant temperature. Furthermore, the layers 3 and 9 in which the plasma collects can be provided with reagents which bring the substances to be detected into a particular state by a time-dependent reaction, i.e. permit a preliminary reaction to take place to completion. One example of this is the activation of creatine kinase with N-acetylcysteine.

Figure 21:
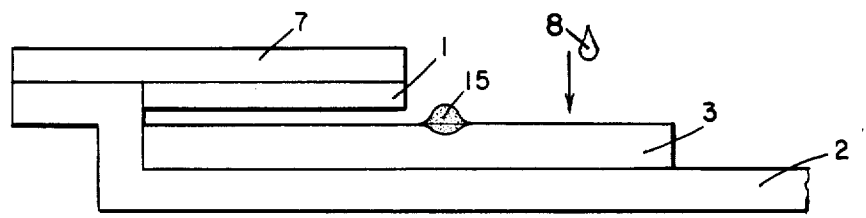
FIG. 21 is an elevation, partly in section, of an eighteenth preferred embodiment.
Figure 22:
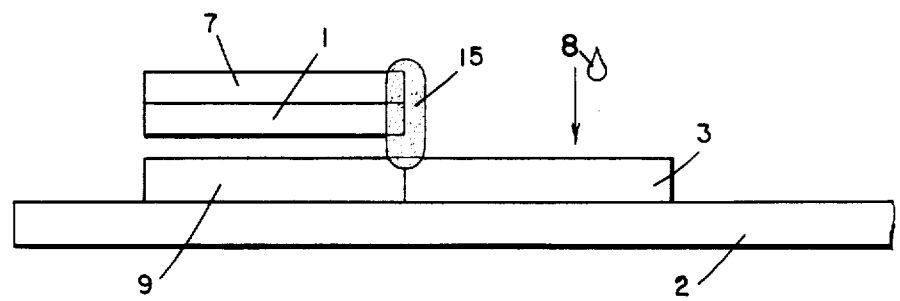
FIG. 22 is an elevation, partly in section, of a nineteeth preferred embodiment.
Figure 23:
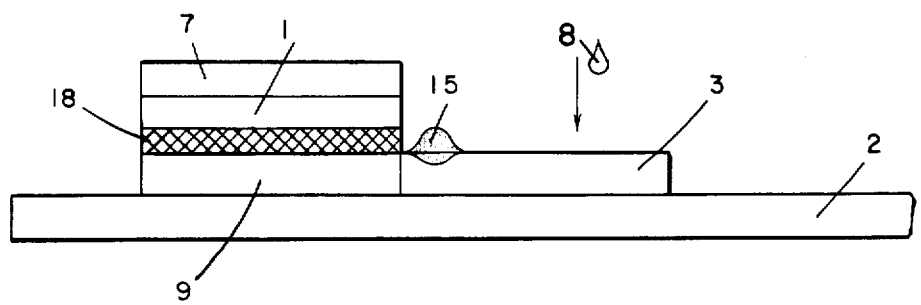
FIG. 23 is an elevation, partly in section, of a twentieth preferred embodiment.

FIGS. 21, 22 and 23 of the accompanying drawings illustrate various possible embodiments of the invention. FIG. 22, the hydrophobic barrier 15 simultaneously serves to secure layers 1 and 7. The description and composition of the other layers correspond to FIGS. 4 to 13.

FIG. 23 illustrates the use of a hydrophobic mesh 18 between the reaction layer 1 and glass fibres 3 or the absorbent layer 9. This hydrophobic mesh protects the arrangement against unintentional slight contact and only permits liquid contact to take place upon applying pressure. This results in an improved practicability.

Figure 24:
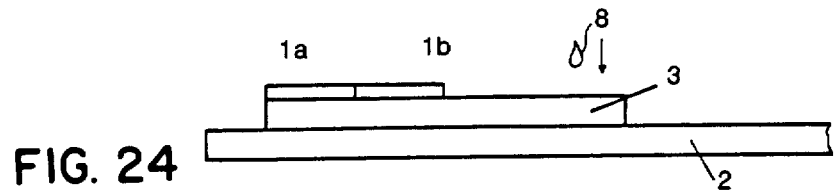
FIG. 24 is an elevation, partly in section, of a twenty-first preferred embodiment.
Figure 25:
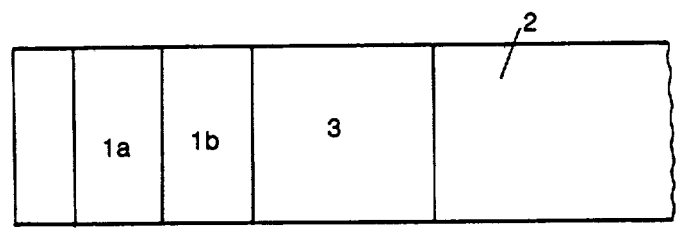
FIG. 25 is a top view of the embodiment shown in FIG. 24.
Figure 26:
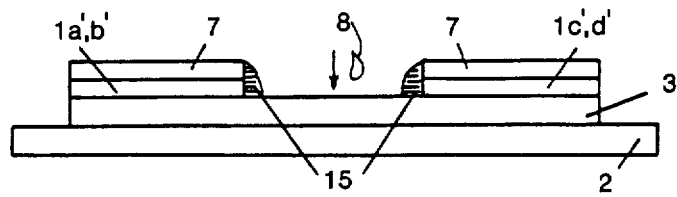
FIG. 26 is an elevation, partly in section, of a twenty-second preferred embodiment.
Figure 27:
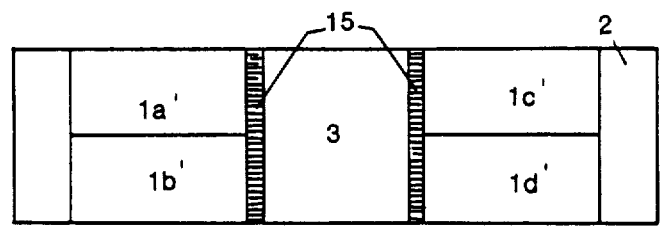
FIG. 27 is a top view of the embodiment shown in FIG. 26.
Figure 28:
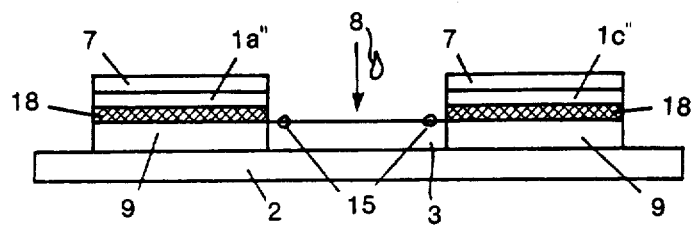
FIG. 28 is an elevation, partly in section, of a twenty-third preferred embodiment.
Figure 29:
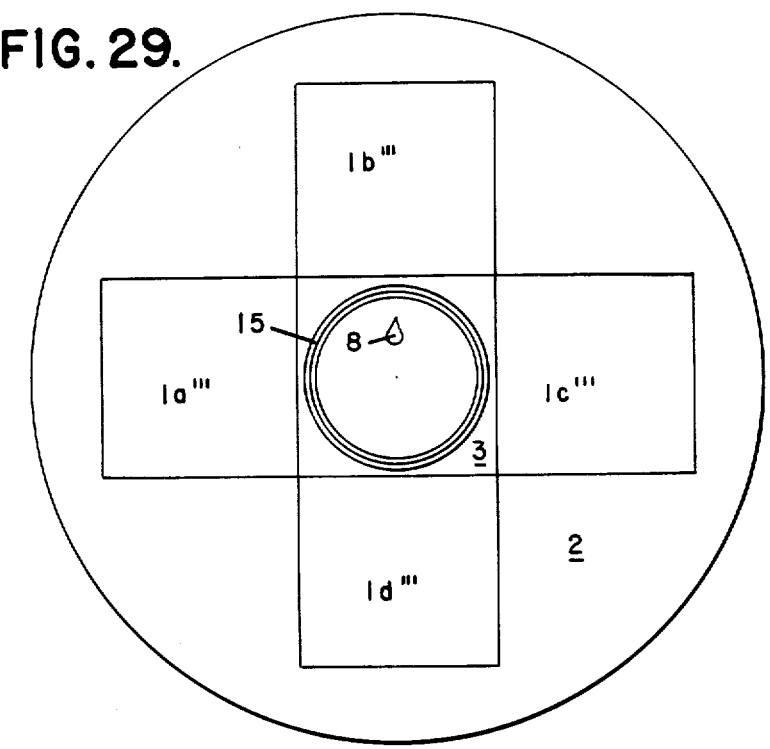
FIG. 29 is a top view of a twenty-fourth preferred embodiment.

Of course, it is possible that the reaction layer 1 consists of two or more different zones (e.g. FIGS. 1 to 3 and 16). These can contain either the same substance in different concentration ranges or different substances when the formulations are appropriately selected. Furthermore, it is also possible to make constructions in which various reaction layers are simultaneously moistened by the plasma emanating from a single point of application (e.g. FIG. 24 et seq.). In this case, a large variety of shapes can be used, such as longitudinal, circular or the like.

FIGS. 24 to 29 of the accompanying drawings illustrate some of these possible arrangements, the various test zones being indicated by 1a to 1d (appropriately primed), the other components corresponding to those of the previously described Figures.

Figure 30:
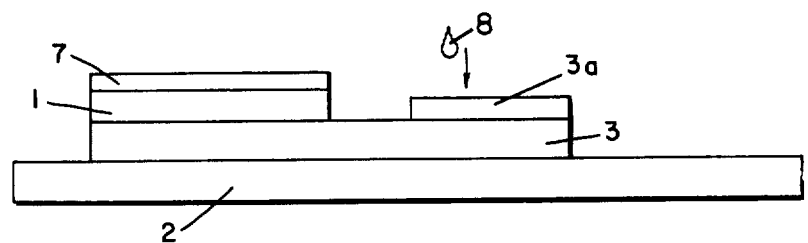
FIG. 30 is an elevation, partly in section, of a twenty-fifth preferred embodiment.
Figure 31:
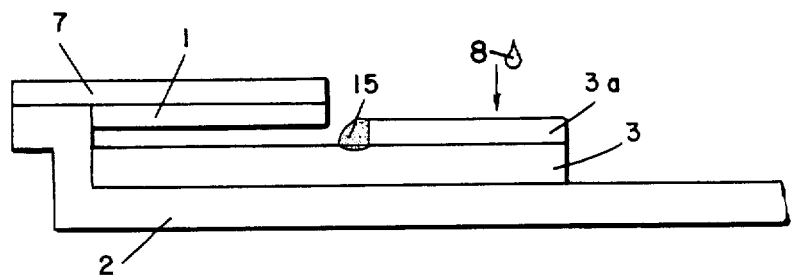
FIG. 31 is an elevation partly in section, of a twenty-sixth preferred embodiment.

Blood separation can also be improved when, a further glass fibre zone 3a is applied as in FIGS. 30 and 31 at that point where blood is dropped thereupon. In this case, layers 3a and 3 can consist of the same material but for 3a a material can be chosen with a different thickness or with a different fibre diameter.

FIGS. 30 and 31 of the accompanying drawings illustrate possible arrangements which otherwise generally correspond to FIGS. 8 and 21.

The following Examples are given for the purpose of illustrating the present invention.

EXAMPLE 1

Cholesterol test strips 0.117 g. methyl hydroxyproylcellulose (Culminal HMPC 8000)
7.000 g. titanium dioxide
0.138 g. monopotassium dihydrogen phosphate
0.479 g. disodium monohydrogen phosphate hydrate
3400 U cholesterol esterase
5000 U cholesterol oxidase
$7 \times 10^4$ U peroxidase
0.476 g. sodium dioctyl sulphosuccinate are dissolved in 70 ml. water. There are then successively homogeneously incorporated 14.0 g. cellulose
8.4 g. polyvinyl propionate dispersion.

Finally, there is added 0.66 g. 3,3',5,5'-tetramethylbenzidine, dissolved in 1.6 ml. acetone.

This batch is coated in an approximately 300μ thick layer on to a smooth synthetic resin film and, after drying at 60°-70° C., cut up into 6 mm. wide strips. Subsequently, these strips, together with a 60μ thick meshwork of nylon and a glass fibre paper (glass fibre filter No. 3362 of Schleicher & Schüll; paper thickness 0.47 mm., density 0.27 g./cm³, average fibre diameter about 2.5μ), also cut up into 6 mm. wide strips, are stuck on to a polyester film. Subsequently, it is cut up into 6 mm. wide strips.

If 40 μl. of blood are applied to the upper side of the test strip and, after 1 minute, the glass fibre with the residual blood is removed, together with the meshwork, by tearing off, then, within 3 minutes, a reaction colour forms on the test zone which corresponds to that which is obtained when, instead of the blood, use is made of plasma centrifuged off from the same blood.

EXAMPLE 2

Cholesterol test 0.45 g. monopotassium dihydrogen phosphate
1.55 g. disodium monohydrogen phosphate hydrate
$1.5 \times 10^4$ U cholesterol esterase
$1 \times 10^4$ U cholesterol oxidase
$3 \times 10^5$ U peroxidase
2.0 g. sodium dioctyl sulphosuccinate
6.9 g. sodium alginate (Algipon)

are dissolved in 250 ml. water and then 2.0 g. 3,3',5,5'-tetramethylbenzidine, dissolved in 15 ml. acetone, are added thereto, whereafter 20.0 g. kieselguhr are homogeneously distributed therein. This reaction mass is applied in 6 mm. wide strips with a silk screen printing machine (fabric: 190μ) on to a glass fibre paper (for example glass fibre filter No. 85/90 of Machery, Nagel & Co.) in the manner described in Example 1. The "printed" glass fibre paper is dried at 60° to 80° C. and then cut up into 12 mm. wide strips in such a manner that the "printed" reaction zone accounts for one half of the strip. This strip is stuck on to the end of the polyester film and this is then cut up into 6 mm. wide strips at right-angles to the glass fibre papers. When 40 μl. of blood are now dropped on to the edge of the uncoated glass fibre paper remote from the reagent layer, the plasma diffuses under the reaction zone. Depending upon the cholesterol concentration of the blood, this reaction zone now assumes a blue reaction colour of differing strong colour. The intensity of the reaction colour corresponds to that which is obtained when, instead of the blood, one uses a serum or plasma obtained from the same blood.

The papers described in the following Table 1 can be used in the same way:

TABLE 1

| Glass fibre papers for plasma separation | | | | | | |
| --- | --- | --- | --- | --- | --- | --- |
| | paper | | | | | |
| manufacturer | type | fibre diameter (μ) | average fibre diameter (μ) | wt. per surface area (g/m²) | thickness (μm) | density (g/cm³) |
| Machery & Nagel | 85/90 BF | 2–9 | 3.2 | 87 | 350 | 0.249 |
| Nuclepore | P300 | 1–3 | 1.5 | 25 | 89 | 0.275 |
| Schleicher & Schüll | No. 9 | 3–4 | 3.4 | 67 | 269 | 0.247 |
| Schleicher & Schüll | 3362 | 1–7 | 2.5 | 127 | 472 | 0.269 |

EXAMPLE 3

Cholesterol test

A reagent mass consisting of
16.0 g. cellulose M+N Ac 10
86.0 g. of a 0.2% solution of methylhydroxypropyl cellulose (Culminal MHCP 8000)
0.32 g. wetting agent (Marlon)
0.68 g. wetting agent (sodium dioctylsulphosuccinate)
12.0 g. polyvinyl propionate dispersion (Propiofan 70 D)
0.48 g. 3,3',5,5'-tetramethylbenzidine
10.0 g. titanium dioxide
9600 U cholesterol esterase
7200 U cholesterol oxidase
$1.04 \times 10^4$ U peroxidase
0.01 g. gallic acid is coated in a thickness of 0.2 mm. on to a hydrophobic polyester fleece (Reemay 2033, du Pont) and dried at 60° C. Subsequently, a 6 mm. wide strip of this coating and a 12 mm. wide strip of glass fibre filter (e.g. Filter 3362 of Schleicher & Schüll) are stuck side by side on a firm plastics strip in such a manner that the glass fibre filter is very close to the coated fleece. When strips of 6 mm. width are cut transversely from this plastics strip, test strips are obtained with which, after dropping about 50 μl. whole blood onto the side of the glass fibre filter remote from the reagent fleece, after a short time only pure plasma passes over to the reagent fleece and results in the formation of a blue reaction colour, the intensity of which increases with the concentration of the cholesterol in the blood.

EXAMPLE 4

Separate recovery of plasma

A synthetic resin vessel which downwardly narrows conically (e.g. a synthetic resin tip with a piston pipette, length 5 cm., thickness 0.5 cm.) is loosely filled two thirds full with glass fibres according to the following Table 2, packing densities of 0.1 to 0.4 g./cm³ being obtained. After the free, upper part has been filled with blood, the serum diffuses into the tip of the vessel. From there, an "end-to-end" capillary of 15 μl. capacity can be filled by attachment to the opening of the pipette tip. The plasma obtained in this manner can now be used directly for any desired analytical process.

TABLE 2

Investigation of the separating ability of various glass fibres in an experimental arrangement according to Example 4.
Glass fibres: properties, separating abilities for erthrocytes/plasma

| Johns-Manville USA | VEB Trisola DDR | diameter (μm) range* | diameter (μm) average value | fibre length μm | Surface area m²/g | separation erythrocytes/plasma |
|---|---|---|---|---|---|---|
| 100 | | 0.2–0.29 | 0.25 | 300 | 5.1 | + |
| 102 | | 0.3–0.33 | 0.32 | | 4.5 | + |
| 104 | | 0.34–0.48 | 0.4 | 800 | 3.12 | + |
| 106 | | 0.49–0.58 | 0.54 | 1000 | 2.6 | +++ |
| | U 60 | 0.51–0.64 | 0.58 | | — | ++ |
| 108A | | 0.59–0.88 | 0.74 | 1200 | 1.72 | ++ |
| | U 70 | 0.65–0.76 | 0.71 | | | ++ |
| | U 80 | 0.77–0.93 | 0.85 | | | +++ |
| | U 90 | 0.94–1.19 | 1.07 | | | ++ |
| | U 100 | 1.2–1.44 | 1.32 | | | +++ |
| 108B | | 0.89–2.16 | 1.53 | | 0.71 | +++ |
| | U 156 | 1.45–2.49 | 1.97 | | — | + |
| 110 | | 2.17–3.10 | 2.6 | | 0.49 | — |
| 112 | | 2.6–3.8 | 3.2 | 1900 | 0.40 | — |
| | F | 2.5–4.0 | 3.3 | | | — |

+ satisfactory;
++ good;
+++ very good;
— negative.
*80% of the fibres lie within this range

EXAMPLE 5

Effects of a hydrophobic barrier

To demonstrate the effects of a hydrophobic barrier 15, an arrangement according to FIG. 14 was assembled comprising a transparent polycarbonate film 2 of 6 mm. width and 0.3 mm. thickness, a 9×6 mm. absorbent layer 9 of 0.09 mm. thick glass fibre paper, a hydrophobic nylon meshwork 18 of 0.075 mm. thickness and a transparent covering film 7. A glass fibre paper 3 is fixed in absorbent contact on to the carrier, which paper 3 consists of a glass fibre paper (Schleicher & Schüll, No. 3362, thickness 0.47 mm.) of 6 mm. width and with the length given in the following Table 3. In each case, one half of these devices are provided on the point of contact between the layers 3, 9 and 18 with an approximately 2 mm. wide and 0.1 mm. thick barrier 15 of paraffin wax.

For the determination of the amount of plasma obtained, on the middle of the glass fibre paper 3 there are applied the amounts of blood indicated in the following Table 3 and, after 30 seconds, the wetting of the absorbent layer 9 is determined, as well as any possible supersaturation (depth of penetration of the erythrocytes into layer 9). The results given in Table 3 show that, due to the hydrophobic barrier, the separation is improved and a complete saturation is achieved so that such a test can be carried out even in the case of very small volumes of blood, for example with capillary blood from a finger tip. In each case, the experiments were carried out five times and the results determined.

TABLE 3

| dimensions of the glass fibre fleece (3) | volume of blood (μl) applied | % wetting of layer 9 with hydrophobic barrier plasma $\overline{X}$ n = 5 | % wetting of layer 9 with hydrophobic barrier blood $\overline{X}$ n = 5 | % wetting of layer 9 without hydrophobic barrier plasma $\overline{X}$ n = 5 | % wetting of layer 9 without hydrophobic barrier blood $\overline{X}$ n = 5 |
|---|---|---|---|---|---|
| 6 × 6 mm. | 25 | 88 | 0 | 77 | 12 |
| | 30 | 97 | 0 | 72 | 22 |
| | 35 | 99 | 0 | 83 | 18 |
| 7 × 6 mm. | 29 | 86 | 0 | 82 | 3 |
| | 35 | 100 | 0 | 87 | 21 |
| | 41 | 100 | 0 | 97 | 31 |
| 8 × 6 mm. | 33 | 96 | 0 | 79 | 0 |
| | 40 | 100 | 0 | 92 | 0 |
| | 47 | 100 | 0 | 100 | 13 |

It will be understood that the specification and examples are illustrative but not limitative of the present invention and that other embodiments within the spirit and scope of the invention will suggest themselves to those skilled in the art.

What is claimed is:

1. A unitary multilayer device for separating plasma or serum from whole blood and analyzing such plasma or serum, comprising:
   (a) a fibrous layer capable of separating blood cells from serum or plasma in a whole blood sample, wherein said fibrous layer contains glass fibers and has a density of from 0.1 to 0.5 g/cm³ and wherein said glass fibres have an average diameter of from 0.2 to 5 microns; and
   (b) a reaction layer which is or may be brought into fluid communication with said fibrous layer while leaving at least a portion of said fibrous layer free from direct attachment to said reaction layer, said reaction layer contaning means for determining a component of plasma or serum.

2. The device of claim 1, further comprising an inert substrate to which said fibrous layer and said reaction layer are attached directly or indirectly.

3. The device of claim 1, wherein said glass fibers have an average diameter of from 0.5 to 2.5 microns.

4. The device of claim 1, wherein said glass fibers have an average diameter of from 0.5 to 1.5 microns.

5. The device of claim 1, wherein said fibrous layer further comprises synthetic resin fibers.

6. The device of claim 1, wherein said reactin layer contains a plurality of layers.

7. The device of claim 1, further comprising an inert carrier between said fibrous layer and said reaction layer which carrier permits passage of plasma or serum into said reaction layer.

8. The device of claim 1, further comprising an inert carrier layer positioned below said reaction layer wherein said reaction layer and said inert carrier are adapted to produce a detection reaction with a component material of plasma or serum which is analyzable or detectable through said inert carrier.

9. Device of claim 1, further comprising a removable layer which supports said glass fiber containing fibrous layer.

10. The device of claim 9, further comprising means for fixing said removable layer to a substrate.

* * * * *